US012740883B2

(12) United States Patent
Mirza et al.

(10) Patent No.: US 12,740,883 B2
(45) **Date of Patent: *Sep. 22, 2026**

(54) WEARABLE SYSTEM FOR EVALUATING JOINT PERFORMANCE AND FUNCTION

(71) Applicant: Kinisi Inc, Santa Cruz, CA (US)

(72) Inventors: Faisal Mohammed Mirza, Aptos, CA (US); Rajveen Rosie Sendher, Santa Cruz, CA (US); Manjirnath Agrahayan Chatterjee, Alameda, CA (US)

(73) Assignee: Kinisi Inc, Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/406,507

(22) Filed: Dec. 2, 2025

(65) Prior Publication Data

US 2026/0102267 A1 Apr. 16, 2026

Related U.S. Application Data

(63) Continuation of application No. 17/351,157, filed on Jun. 17, 2021, now Pat. No. 12,514,727.

(Continued)

(51) Int. Cl.
*A61F 5/01* (2006.01)
*A61B 5/00* (2006.01)

(Continued)

(52) U.S. Cl.
CPC ............ *A61F 5/0109* (2013.01); *A61B 5/024* (2013.01); *A61B 5/14532* (2013.01);

(Continued)

(58) Field of Classification Search
CPC .. A61F 5/00; A61F 5/01; A61F 5/0102; A61F 5/0104; A61F 5/0106;

(Continued)

(56) References Cited

U.S. PATENT DOCUMENTS 10,758,673 B2 9/2020 Hyde et al.
2007/0107778 A1 5/2007 Bettin et al.

(Continued)

FOREIGN PATENT DOCUMENTS

EP 1814500 B1 * 6/2008 ........... A61F 13/085
KR 101308973 B1 * 9/2013 ........... A61B 5/4538

OTHER PUBLICATIONS

Cleveland Clinic, Thigh Muscles, Apr. 11, 2025.*

(Continued)

*Primary Examiner* — Alireza Nia
*Assistant Examiner* — Andrew Jun-Wai Mok
(74) *Attorney, Agent, or Firm* — Fenwick & West LLP

(57) ABSTRACT

One embodiment of a disclosed wearable device includes a pliable wrap with a plurality of fluid chambers stitched together to structure the wrap to conform to a shape of a joint of the user. An array of tension sensors are embedded into the wrap across one or more horizontal axes and one or more vertical axes of the wrap. Each tension sensor in the array detects forces exerted by the joint covered by the wrap and is connected with at least one adjacent tension sensor by a conductive thread. The wrap is further embedded with a controller, which receives signals representing movements detected by tension sensors of the array and generates a signal to activate the electroactive gel in one or more fluid chambers based on an analysis of the received signals.

20 Claims, 9 Drawing Sheets

*Knee Wrap*
200

Related U.S. Application Data

(60) Provisional application No. 63/041,627, filed on Jun. 19, 2020.

(51) Int. Cl.
*A61B 5/024* (2006.01)
*A61B 5/145* (2006.01)

(52) U.S. Cl.
CPC ........ *A61B 5/14542* (2013.01); *A61B 5/4585* (2013.01); *A61B 5/4839* (2013.01); *A61B 5/6812* (2013.01); *A61B 2562/066* (2013.01); *A61F 2005/0188* (2013.01)

(58) Field of Classification Search
CPC ...... A61F 5/0109; A61F 5/05816; A61F 5/34; A61F 5/012; A61H 2201/5053; A61H 2201/5056; A61H 2201/5058; A61H 2201/5061; A61H 2201/5064; A61H 2201/5071; A61B 2562/06; A61B 2562/066; A61B 5/00; A61B 5/45; A61B 5/4538; A61B 5/4585; A61B 5/6801; A61B 5/6802; A61B 5/6812; A61B 5/6813; A61B 5/6828
See application file for complete search history.

(56) References Cited

U.S. PATENT DOCUMENTS

| | | | | |
|---|---|---|---|---|
| 2009/0024065 | A1 | 1/2009 | Einarsson | |
| 2011/0066091 | A1 | 3/2011 | Larson et al. | |
| 2015/0088043 | A1* | 3/2015 | Goldfield | A61F 5/01 602/6 |
| 2015/0182410 | A1 | 7/2015 | Burris et al. | |
| 2016/0120733 | A1* | 5/2016 | Ishikawa | A61B 5/6824 36/43 |
| 2017/0258995 | A1 | 9/2017 | Hyde et al. | |
| 2018/0146721 | A1 | 5/2018 | Aherne et al. | |
| 2019/0117156 | A1 | 4/2019 | Howard et al. | |

OTHER PUBLICATIONS

Physiopedia, Gastrocnemius, Mar. 7, 2025.*
Kim K, Monitoring Method of Motion Danger, Seo. 17, 2013.*
Kim K, Monitoring Method of Motion Danger, Sep. 17, 2013.
Lou et al."Recent Advances in Smart Wearable Sensing Systems " Advanced Materials Technologies, vol. 3, No. 12, (1800444), pp. 1-17 (Year 2018).
United States Office Action, U.S. Appl. No. 17/485,206, filed Oct. 28, 2025, 38 pages.
United States Office Action, U.S. Appl. No. 17/351,157, dated Sep. 3, 2025, 22 pages.

* cited by examiner

*Digital Brace System*
100

*Knee Wrap*
200

*Tension Sensor Array*
300

*Knee Wrap*
350

*Knee Wrap*
350

Knee Wrap
400

*Knee Wrap*
500

Knee Wrap
600

WEARABLE SYSTEM FOR EVALUATING JOINT PERFORMANCE AND FUNCTION

CROSS REFERENCE TO RELATED APPLICATIONS

This application is a continuation of prior, co-pending U.S. application Ser. No. 17/351,157, filed on Jun. 17, 2021, which claims the benefit of U.S. Provisional Ser. No. 63/041,627, filed on Jun. 19, 2020, both of which are incorporated herein in their entirety for all purposes.

TECHNICAL FIELD

The disclosure relates generally to a knee brace and, more specifically, to a form fitting knee brace integrated with a digital system for evaluating and monitoring the knee of a wearer.

BACKGROUND

Conventional flexible knee sleeves merely provide soft tissue support in the form of a wrap or fabric covering the knee. Although there are variations in the design, fabric, size, and support provided by such braces, they all passively providing comfort to the knee, but do not actually collect data regarding the condition, performance, movement, or function of the knee. Additionally, conventional rigid knee braces limit the range of motion of the knee. Additionally, these conventional braces are similarly incapable for collecting data regarding the knee because they are incompatible with sensors on collecting data on the knee or body of a wearer. That is, these braces do not adjust their functionality or performance based on feedback describing the current condition or performance of the knee. Additionally, because they are designed to accommodate typical use by a wearer and typical injury patterns, conventional rigid braces restrain a wearer's movement without regard for the patient's specific condition because they are designed to accommodate typical use by a wearer and typical injury patterns.

Further, conventional techniques and tools for evaluating the performance or function of a knee do not provide automatic and continuous feedback nor do they enable real-time adjustments to a knee brace. Measurements performed by tools such as a goniometer must be taken manually and are not designed to continuously collect data while a subject moves freely. Even in laboratories, electronic motion sensors only measure the motion of the knee in a single direction (i.e., flexion and extension) but are not designed for use during recreational activities given their cumbersome size. Other conventional wearable sensors, which describe the performance of the knee based on the relative motion of the leg to the thigh, are inaccurate and imprecise for calibrating the kinematic function of the knee.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

I. Overview

A digital brace system characterizes the motion of the joint itself and the body around the joint, for example by measuring the angular displacement of the joint in a particular plane or the pressure and force on the joint. In addition, as a user moves while wearing the brace, sensors integrated into the brace measure changes in physiological properties of the body around the joint and the joint itself. Such measurements and data may be stored locally on a controller embedded into the brace or remotely at a server in communication with the controller embedded into the brace.

The comprehensive data captured by the sensors provides precise information on gross and subtle movements of the joint and parts of the body surrounding the joint to provide feedback for adjusting the brace in real-time or near real-time to optimize movement of the joint, prevent injury, or further augment performance of the joint in manner that conventional braces are incapable of. In particular, the brace includes additional components and elements that allow the brace to adjust its shape to accommodate the movement of the joint or to deliver a combination of nutrients to the user to maintain or improve the performance of the joint. The digital brace system described herein may be used in parallel with pertinent treatments to evaluate joint function over a long period of time.

II. System Configuration

Figure 1:
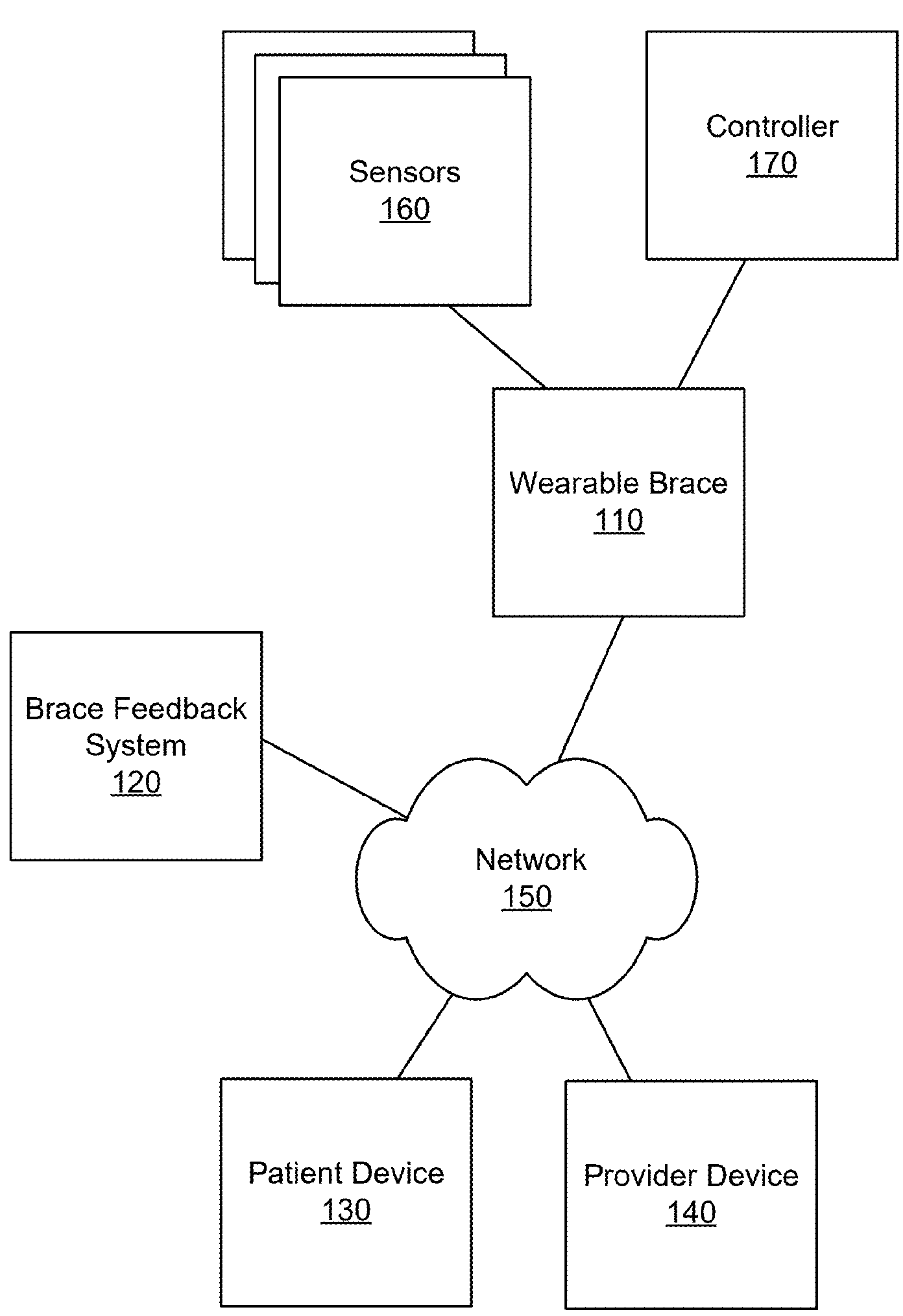
FIG. 1 illustrates a system architecture for a digital brace system, according to one example embodiment.

FIG. 1 illustrates a system architecture for a digital brace system, according to one example embodiment. The digital brace system 100 may includes a wearable brace 110, a device feedback system 120, a patient device 130, a provider device 140, and a network 150. The wearable brace further includes one or more sensors 160 and a controller 170 embedded into the brace. Although FIG. 1 illustrates only a single instance of most of components of the digital brace system 100, in practice more than one of each component may be present, and additional or fewer components may be used.

The wearable brace 110 is a device which a user may wear around any joint to monitor, maintain, or improve the performance and function of the joint. The wearable brace 110 is designed with a pliable material, also referred to herein as "a plyowrap" or more simply "a wrap," that is capable of adapting to the dynamic movement of the joint without inhibiting the movement of the joint. The plyowrap may be structured in a variety of ways, for example, as a rectangular structure that wraps around a knee or a sleeve that is pulled up to the knee from the foot. Alternative embodiments of the plyowrap of the wearable brace 110 are additionally described herein.

Sensors 160 are embedded within the brace 110 to collect data describing various aspects of the motion of the joint and to characterize the movement of the joint based on kinematic information and gait information determined from the collected sensor data. The sensors 160 may be embedded into the wearable brace 110 by weaving them into the pliable wrap of the brace 110 or any other suitable material integration technique. In alternate embodiments, the sensors 160 are attached to the plyowrap using an adhesive or any other suitable attachment technique. In embodiments where the brace 110 is worn over the knee of a user, the sensors 160 additionally collect balance information of the tibio-femoral and tibio-fibular patellofemoral movements.

The controller 170 receives signals from the sensors 160 describing physiological properties of the user and the joint including, but not limited to temperature, $O_2$ saturation, glucose, energy, heat, elasticity, vibration, blood pressure, heart rate, conductivity, sensitivity, ultrasonic impedance, electromagnetic frequency, chemistry, or any other suitable physical or physiological properties, and changes in those physiological properties. Based on the received signals, the controller 170 encodes instructions for adjusting the wearable brace 110 into electronic signals and transmits those signals to other components of the wearable brace 110. As an example, the controller 170 may transmit an electronic signal that causes fluid chambers in the plyowrap to change geometry to increase or decrease the pliability of the plyowrap. As another example, the controller 170 may transmit electronic signals that cause fluid chambers in the plyowrap to change permeability to enable transdermal delivery of nutrients stored within the fluid chambers.

The design and functionality of the wearable brace 110, the sensors 160, and the controller 170 are further discussed below with reference to FIGS. 2-7.

When the wearable brace 110 is worn around a joint to measure neuromusculoskeletal function, the brace feedback system 120 analyzes movements of the joint based on changes in a contour digital map describing the movement and performance of the joint over time, measurements recorded by wired and wireless sensors, or a combination thereof. The brace feedback system 120 may analyze the measured data to represent the knee visually as an image (or an animation) or computationally in a dataset (or a pattern). In embodiments involving computational representations of the measured data, the datasets and patterns are collected sequentially and serially over time to provide analytics of the knee, which may be reviewed by a patient or medical provider. Alternatively, the collected analytics may be used as a basis for further individual and comparative analysis and pattern recognition. Applicable analytics techniques include, but are not limited to, cognitive learning, machine learning, augmented reality, and virtual reality systems. In embodiments where larger datasets of multiple individuals are available to the brace feedback system 120, the brace feedback system 120 may be trained to predict the likelihood of a joint injury and to evaluate the performance of the joint based on patterns, characteristics, and outcomes derived from the larger dataset of multiple individuals. In alternate embodiments, the functionality described with reference to the brace feedback system 120 may be performed locally by the controller 170 and the data collected by the sensors 160 may be stored locally by the controller 170.

In some embodiments, the brace feedback system 120 may communicate with a patient device 130, a provider device 140, or both to display real-time feedback collected from the wearable brace to a user, a coach, a trainer, a therapist, or another third party. The data collected by the wearable brace 110 may provide an image of the movement of the knee in real-time with quantitative data and visually interpretable qualitative patterns of motion, which may be processed into a computational representation of the motion of the user's knee. The brace feedback system 120 may perform comparative analytics of the visual representations through any suitable technique including, but not limited to, computational, applied, analytic, or interpreted techniques, algorithmic learning, machine learning, artificial intelligence, or any other suitable technique. The brace feedback system 120 may visually display motion captured patterns of the anatomical movements of the knee using wire frame models or other computational 3D models of the actual knee motion. Accordingly, the brace feedback system 120 may develop or compute a representative model of the knee, which characterizes both the form and function of the knee in real-time.

In one embodiment, the brace feedback system 120 displays feedback using a color-coded system. A display of a first color (e.g., green) indicates that the pattern of motion is normally distributed with no tension or constraint beyond a set of normalized parameters. A display of a second color (e.g., yellow) indicates the presence of one or more tension or vibration parameters and suggests that the user should use caution to avoid risking an injury, falling, or further damaging the review joint. Alternatively, or in addition to, the display of the second color may indicate that an adjustment to the wearable brace 110 may be necessary.

The brace feedback system 120 may additionally generate predictions using the motion data captured by the wearable brace 110, which includes the rotation, translation, glide, tilt, pressure, forces, velocity, and acceleration of the various anatomic components of the joint in space and relative to other anatomic components of the joint. The brace feedback system 120 may generate predictions based on the overall pattern of motion based on measures and analyses repeated over time for a particular user in a non-injured state or alternate control state. The pattern of motion recorded for the joint may be correlated with physiologic parameters, which may be measured by physiological sensors in the wearable brace 110 (not shown) or determined based on threshold parameters determined from previously collected data and analyses.

For the sake of simplicity, embodiments of the digital brace system 100, and more specifically the wearable brace 110, are described herein with reference to a knee brace, but a person having ordinary skill in the art would appreciate that the described digital brace system 100 may be used to monitor the performance and function of any joint of the human body.

In some embodiments (not shown), a single user may wear multiple wearable braces 110, for example braces 110 on both knees. In such embodiments, data recorded by each brace 110 may be aggregated into a combined dataset, which the brace feedback system 120 may use for a more holistic assessment of the user's body. The brace feedback system 120 may use the data in the combined dataset to perform a coordinated assessment of the user's motion, performance, and health.

The patient device 130 is a computing device through which a user wearing the brace 110 may interact with the digital brace system 100. Similarly, the provider device 140 is a computing device through which a medical provider or third-party entity overseeing the user wearing the brace 110 may interact with the digital brace system 100. The patient device 130 and the provider device 140 may be computer systems. An example physical implementation of such a system is more completely described with FIG. 7. Each of the patient device 130 and the provider device 140 are configured to communicate with the controller 170, the device feedback system 120, or both via the network 150. For example, via a wireless application stored on the patient device 130, a user can communicate instructions for the controller 170 to adjust the shape of the wearable brace 110 or to deliver particular nutrients to the user.

The patient device 130 may also store third-party health monitoring applications that monitor various related aspects of the health of a user. The wearable device 110 and the brace feedback system 120 may communicate with such third-party applications to gain further insight into a patient's health. For example, a third-party application stored on the patient device 130 may communicate with a heart rate monitor on the patient's chest. Accordingly, the digital brace system 100, and more specifically the brace feedback system 120 and the wearable brace 110, may synchronize with the third party application to determine when the patient is in discomfort or is experiencing a symptom and supplement the data collected by the sensors with those determinations.

Similarly, a provider, trainer, or supervisor of the user may operate the provider device 140 to communicate instructions to the controller based on feedback or data recorded by the sensors 160. Accordingly, the wearable brace 110 may be used as a diagnostic tool by healthcare providers who monitor data received from physiology sensors embedded in the plyowrap.

Examples of other users operating a provider device 140 include, but are not limited to, an employer, a technician, a caregiver, a trainer, a coach, a physical therapist, a doctor, or a health care worker. The communication between the patient device 130 and the provider device 140 and other components of the digital brace system 100 may be wireless, for example, via a short-range communication protocol such as Bluetooth, cellular, Wi-Fi, Ant, Zigbee, or any other suitable wireless connection.

The network 150 represents the various wired and wireless communication pathways between the wearable brace 110, the device feedback system 120, the patient device 130, and the provider device 140 via network 150. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), a custom binary encoding etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above. The network 150 may enable components of the digital brace system 100 to communicate using wireless connections, for example Bluetooth, cellular, Wi-Fi, Ant, Zigbee, or any other suitable wireless connection.

III. Structure of the Wearable Brace

To use the wearable device, a user secures a "plyowrap," around the joint of interest. As discussed above, the plyowrap may be worn over any joint of the body, for example the knee, the elbow, the wrist, or any other suitable joint. For illustrative purposes, the following description discusses embodiments in which a plyowrap is used to cover the knee of a user, hereafter referred to as a "knee wrap." However, a person having ordinary skill in the art would appreciate that the description included herein may be applied to a plyowrap used to cover any other joint.

When worn by a user to cover any suitable joint, the wearable brace 110 will collect data regarding the performance and functionality of the joint itself and parts of the body surrounding the joint. In some embodiments, the plyowrap is a tubular sleeve that may be pulled over the joint using anatomic features surrounding the joint to guide the placement and fit of the plyowrap. In such embodiments, the plyowrap may include graphic markers describing the anatomic orientation of the plyowrap. Alternatively, the plyowrap may be worn by folding the plyowrap over the joint using a securing mechanism to secure the plyowrap in place, for example a buckle, a clasp, a removable adhesive, or any other suitable securing mechanism.

In embodiments where the wearable brace is a knee brace, the placement and fit of the plyowrap may be guided using some combination of the patella, tibial tubercle, the medial and lateral condyles, and any other suitable anatomic features of the knee. In embodiments of a knee wrap, for example the knee wrap 350 illustrated in FIG. 3C, the wrap 350 may include an opening or a socket to accommodate the position of the patella within the wrap 350. The knee wrap may further be designed to expose the back of the knee to improve the comfort of the user. The knee wrap may additionally be designed with vent holes in the area of the wrap covering the knee or any other body part around the knee to improve the breathability of the wrap.

The flexible, pliable material of the wrap enables the plyowrap, when worn, to conform to the shape of the joint of the user. Given the pliable nature of the material, the size and geometry of the plyowrap may vary depending on how the plyowrap is stretched based on size of the joint covered by the plyowrap and the movement of the joint covered by the plyowrap. In some embodiments, the circumference of the plyowrap is initially 5 centimeters before being stretched. Similarly, the cross-sectional thickness of the plyowrap may vary depending on the joint being covered, the size of the joint being covered, or the purpose for which the plyowrap is being used. In other embodiments, the plyowrap may be designed to accommodate a particular body type (e.g., toddlers, children, adults) or a particular user (e.g., a wrap customized for the user).

The flexible, pliable material of the plyowrap may be a natural or synthetic fabric or set of woven fabrics. As an example, the material may be a blend of materials including, but not limited to, neoprene, lycra, viscose, polyester, rubber, and natural fibers such as silk, cotton, hemp, or wool. The plyowrap may further be breathable, moisture wicking, moisture resistant, moisture repellant, or a combination thereof. In some embodiments, the knee wrap is electrically conductive. Alternatively, particular components of the knee wrap may be conductive.

In some embodiments, a support structure is integrated into the material of the plyowrap to provide additional support to the joint covered by the plyowrap. The support structure may be rigid and durable enough to prevent unexpected or damaging movements of the joint, but malleable enough to allow the plyowrap to conform to natural movements of the joint within the plyowrap. The support structure may have mechanical, hydraulic, electrochemical, electrical, and magnetic properties, or some combination thereof. In some embodiments, the support structure is a component covering some or all of the joint (e.g., a plastic, a metal, or any other suitable material). Alternatively, the support structure may be a semi-rigid strap wrapped around the joint. In some embodiments, the rigid properties of the support structure may be activated by an electrical signal indicating that the joint is moving beyond an acceptable or safe range of motion. The electrical signal may cause the support structure to adjust its position, shape, geometry, or pliability to prevent the joint from moving beyond the acceptable range of motion. In such embodiments, the support structure may include an electroactive gel or ferrofluid, which responds to the activation signal to adjust the properties of the support structure. Electroactive gels and ferrofluids are further discussed below with reference to FIG. 4.

Figure 2:
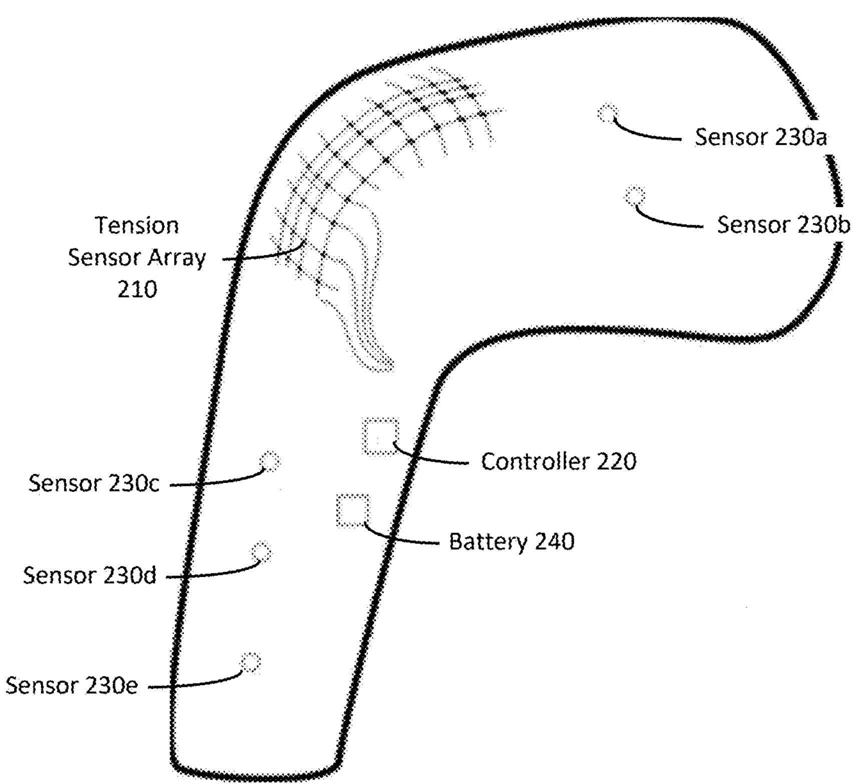
FIG. 2 is an illustration of a knee wrap that includes a combination of electronic components that detect and analyze movements of the knee, according to one example embodiment.

To evaluate the performance and functionality of the joint covered by the plyowrap, the plyowrap is integrated with an array of sensors configured to measure and monitor the movement of the joint while the user wears the plyowrap. In some embodiments, the array of sensors characterizes the movement of the joint within the plyowrap based on how the plyowrap stretches or deforms due to the movement of the joint. FIG. 2 is an illustration of a knee wrap that includes a combination of electronic components that detect and analyze movements of the knee, according to one example embodiment. In the illustrated embodiment, the knee wrap 200 includes a tension sensor array 210, a controller 220, one or more sensors 230 (e.g., 230), and a battery 240 (or other power source). The knee wrap, for example the knee wrap 200, may also include a communication circuit (or chip) (e.g., WiFi or Bluetooth). The communication circuit 220 may be integrated with or communicatively coupled with the controller 220.

The tension sensor array 210 monitors the movements of the knee within the knee wrap 200. As illustrated in FIG. 2, tension sensors of the array 210 are arranged in a grid pattern along vertical and horizontal axes of the plyowrap. In such embodiments, the vertical and horizontal tension sensors create a Cartesian map around the knee, which may be used to monitor displacement, angular movements, and rotation of the knee. The Cartesian map of sensors relays information about changes in the polygon shape of the knee during movement of the knee, which may be converted into a model of the kinematics of knee using machine-learning techniques or any other suitable computational technique.

In the illustrated embodiment, the array 210 covers only the knee of the user. In one embodiment, each tension sensor of the array 210 is a sensor wire or a stretchable, tension meter. When the user moves their knee, the movement of the knee causes the tension sensors of the array 210 to stretch and generate signals describing the elastic movement of each tension sensor. Accordingly, the tension sensor array 210 may be used to measure properties of the joint including, but not limited to, displacement, elasticity, fatigue strength, instability, swelling, forces or pressure across the surface of the joint, the strength of dynamic stabilizers of the joint, acceleration and velocity of movements of the joint, and patterns of mobility based on joint and gait kinematics detected as the joint moves in real-time.

Additionally, tension sensors of the tension sensor array 210 are attached to the sleeve in such a manner that movement of the knee does not displace or dislocate individual tension sensors from their attachment sites in the array 210. The elastic properties of the pliable wrap and sensors of the array 210 allow both components to return to their initial geometry after being stretched or undergoing a deformation. Accordingly, the tension sensor array 210 may continuously track displacements and deformations caused by the movement of the knee over time. The tension sensor array 210 is further discussed below with reference to FIGS. 3A-C.

The controller 220, which is an embodiment of the controller 170, is a type of computer processing unit. The controller 220 receives signals from the tension sensor array 210 describing the movement of the tension sensors and extrapolates the movement of the knee from the elastic movements of the tension sensors. The controller 220 may be any suitable circuit board, integrated circuit chip or communication panel configured to process and transmit signals encoded with measurements recorded by the tension sensor array 210. For example, the contraction of a thigh during physical activity may cause a particular group of tension sensors of the array 210 to stretch or contract in response to changes in the geometry or shape of the quadriceps muscle resulting from the contraction. Measurements recorded by an elastic sensor of the array 210 (e.g., voltage measurement recorded by voltage sensors or tension measurements recorded by tension sensors) may be calibrated based on the distance that the sensor was stretched, for example due to flexion or vagus or varus tilt. Sensors of the sensor array 210 may be calibrated during the design of the knee wrap or at any point before a user begins using or wearing the knee wrap.

Other sensors of the array 210 or sensors embedded elsewhere in the knee wrap 200, (e.g., accelerometers and positioning sensors) may measure velocity, direction, location, or any other relevant characteristic of the movement of the knee. The movement of the knee or a representation of the movement of the knee may be extrapolated from measurements recorded by the sensor array 210 using machine-learned models, algorithms, or any other suitable computational tool. In some embodiments, the controller 220 compares data measured by the array 210 for a particular user with a normalized dataset and patterns of motion to compare the performance of the user's joint with varying segments and demographics of populations or individuals.

The controller 220 may be embedded into the knee wrap 200 or integrated in a removable manner. In some embodiments (not shown) the controller 220 is contained in a housing structure, which may be embedded or removably integrated into the knee wrap to improve the durability of the controller 220 and prevent damage to the controller.

A battery 240 is additionally embedded into the knee wrap 200 to power other electrical components of the wrap 200, for example the sensor array 210, the controller 220, and the sensors 230. The battery 240 may be a rechargeable battery or a disposable battery. The battery 240 may be fixed within the wrap 200 and have a recharging port. Alternately, the battery may be removable from the wrap 200 such that a user or provider may replace the battery 240 and connect the electrical components to a new battery. In some embodiments, the battery 240 itself and/or the connections between other electrical components and the battery are waterproof.

In the illustrated embodiment of FIG. 2, the knee wrap 200 further includes five sensors 230 in this example—sensors 230*a*, 230*b*, 230*c*, 230*d*, and 230*e*—which are embedded into the wrap 200. Whereas measurements by the tension sensor array 210 characterize the movement of the knee within the knee wrap 200, the sensors 230 measure physiological properties of the body around the knee and the knee itself. Physiological sensors are further discussed below with reference to FIG. 5.

Figure 3A:
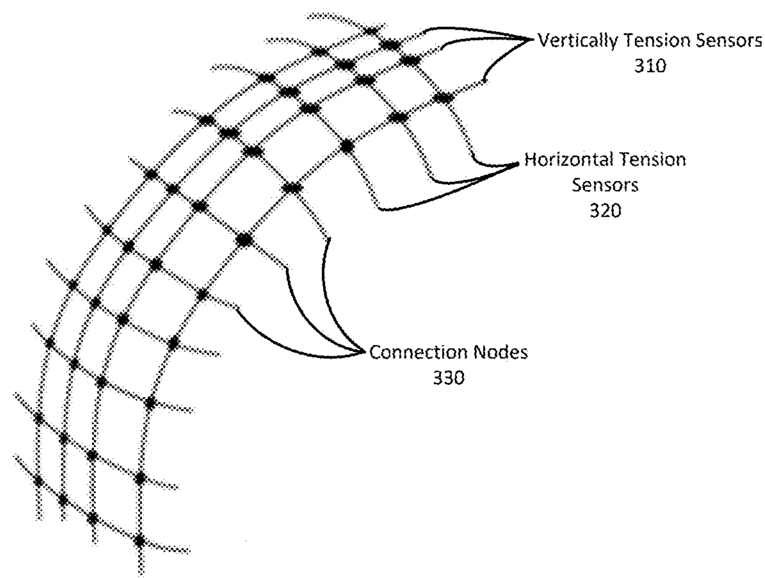
FIG. 3A is an illustration of an array of tension sensors used to detect movements of the knee, according to one example embodiment.

FIG. 3A is an illustration of an array of tension sensors (e.g., pressure sensor matrix) used to detect movements of the knee, according to one example embodiment. The tension sensor array 300 includes one or more vertical tension sensors 310, one or more horizontal tension sensors 320, and connection nodes 330 where a vertical tension sensor 310 intersects with a horizontal tension sensor 230. Each end of the vertical tension sensors 310 and the horizontal tension sensors 320 connect with the controller 220 (or other processing unit).

The tension sensor array 300 detects movements by the knee in any direction as a shifts in the geometry of the sleeve. As the knee moves within the plyowrap, the geometry of the plyowrap also changes given the pliability of the plyowrap. The tension sensor array 300 detects such changes in the geometry of the plyowrap when one or more tension sensors of the array 300 are stretched or compressed with the changing geometry of the plyowrap. Accordingly, signals transmitted by the tension sensor array 300 covering the knee may be interpreted as characterizing movements of the knee within the plyowrap.

As discussed above, tension sensors in the array 300 may be arranged in a grid pattern that spans over the knee. In the illustrated embodiment of FIG. 3A, tension sensors of the array 300 are oriented across both vertical and horizontal axes of the plyowrap such that vertically oriented tension sensor intersects with horizontally oriented sensor. As described herein, the intersection between a vertical tension sensor 310 and a horizontal tension sensor 320 is referred to as a "connection node." As described herein, a connection node is a region of the sleeve with a concentration of circuits or sensors. The concentration of circuits or sensors at a connection node create a matrix of force measurements recorded over a large surface area, which may be used by the controller 220 or the brace feedback system 120 to generate a model of knee displacement and evaluate the movement of the knee based on the pattern of force displacement measured across connection nodes.

In the illustrated embodiment, sensors of the array 300 intersect at connection nodes 330 in a manner that conducts an electromagnetic field or transmits collective signals to a controller. Accordingly, connection nodes 330 represent regions of electrical connectivity between conductive components of the plyowrap. Connection nodes 330 may act as electrical conduits or transmit signals to a controller, for example the controller 170, for processing. For example, a signal carried by a conductive thread may describe the condition of a joint on multiple sides of the joint. The signal transmitted through connection nodes may include instructions for other parts of the knee wrap to react to the current condition of the joint, for example instructions for parts of the plyowrap to become more pliable, for parts of the plyowrap to become more firm, or both. In addition or as an alternative, signals transmitted by a connection node may describe the concentration of forces, the movement of voltages.

In alternate embodiments, the array of tension sensors may be arranged according to a different geometry, for example an alternatively shaped or angled pattern, such that vertical tension sensors 310 and horizontal tension sensors 320 overlap and intersect in a manner other than that illustrated in FIG. 3A.

In alternate embodiments (not shown), tension sensors of the array 210 may be replaced with stretchable voltage sensitive bands, conductive fibers woven into the material of the pliable wrap, or any other suitable elastic sensor. In embodiments where a wrap is embedded with voltage sensitive bands, a change in geometry of a muscle such as a quadriceps muscle during a thigh contraction may be characterized by a voltage change.

In some embodiments, tension sensors of the tension sensor array 310 are anchored in place by circuit bands lining the knee wrap. Each end of a tension sensor may be anchored independently by a circuit band embedded into a wrap. Alternatively, each end of the tension sensor may be integrated into a circuit contained in the circuit band. In some embodiments, circuit bands, such as the lateral bands 360, are circuits into which sensors of the tension sensor array 300 are integrated. In alternate embodiments, the circuit bands are designed from plyoplastic materials or fabrics to transmit sensor data, current, voltage, or any other relevant signal.

Figure 3B:
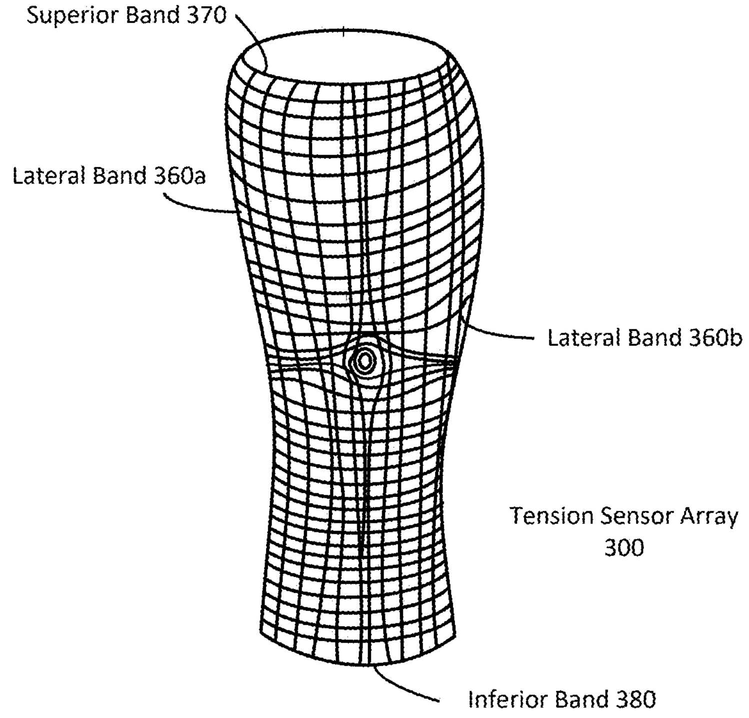
FIGS. 3B-C are illustrations of a knee wrap with an array of the tension sensors anchored by a combination of circuit bands embedded into the knee wrap, according to one example embodiment

FIG. 3B is an illustration of a knee wrap 350 with an array of the tension sensors anchored by a combination of circuit bands integrated into the knee wrap, according to one example embodiment. The knee wrap 350 includes one or more lateral bands 360 (e.g, 360*a-b*), a superior band 370, and an inferior band. The lateral band 360 anchors one end of the horizontal sensors of the tension sensor array 300. As illustrated in FIG. 3B, the lateral band 360 spans the vertical length of the wrap 350. In embodiments where each horizontal tension sensors lines the entire circumference of the wrap 350, both ends of each horizontal tension sensors are attached to a single lateral band. In other embodiments (not shown) the knee wrap 350 may additionally include a second lateral band 360 positioned on the opposite side of the wrap 350 to anchor the opposite end of the tension sensors. In additional to the linear bands illustrated in FIG. 3B, circuit bands may be designed in any other suitable geometry or shape.

The superior band 370 and the inferior band 380 anchor vertical tension sensors of the tension sensor array 300. As illustrated in FIG. 3B, the superior band 370 and the inferior band 380 each span a horizontal length of the wrap 350. The superior band 370 is embedded into a wrap such that the superior band anchors the upper end of vertical tension sensors (e.g., the end of a vertical tension sensor positioned above the joint covered by the wrap 350). In comparison, the inferior band 380 is embedded into a wrap such that the inferior band anchors the lower end of the vertical tension sensors (e.g., the end of the vertical tension sensors positioned below the joint covered by the wrap). The inferior band may be structurally and functionally similar to the superior band. In some embodiments, the tension sensors are only anchored by a superior lateral band positioned above knee. In some embodiments, the superior band 370 and the inferior band 380 themselves contain one or more tension sensors, voltage sensors, stretch sensors, or any other suitable elastic sensor, which allow the bands 370 and 380 to characterize movements of the part of the body covered by each band.

Compared to the embodiment illustrated in FIG. 2, the knee wrap 350 example in FIG. 3B includes a tension sensor array 310 that spans the full length of the wrap 350. Accordingly, the tension sensor array 310 may be used to measure the movement of the knee within the brace as well as movements of other body parts covered by the wrap 350, for example the lower thigh and upper shin.

Figure 3C:
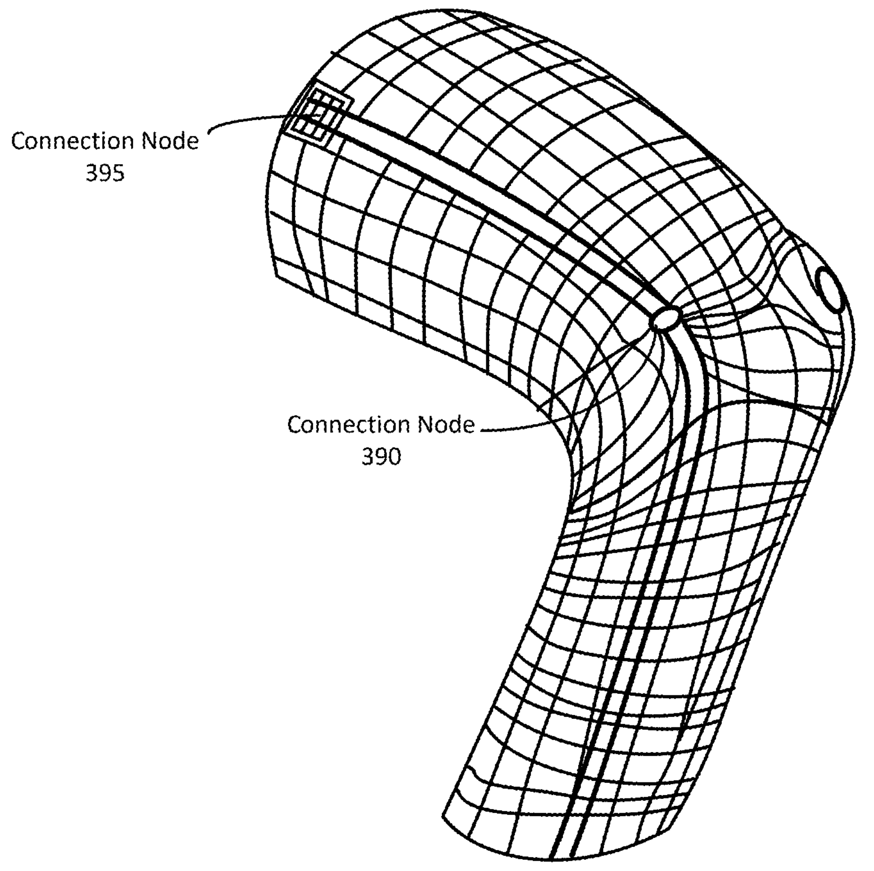

FIG. 3C is an illustration of a knee wrap worn by a user bending their knee, according to one example embodiment. Continuing from the description above of the knee wrap 350, FIG. 3C illustrates a lateral view of the pliable knee wrap 350. Depending on the arrangement of tension sensors in the array 310, the number of tension sensors intersecting at a connection node my vary depending on the position of the connection node on the wrap 350. For example, the number of tension sensors intersecting at the connection node 390 is greater than other connection nodes of the knee wrap 350. Accordingly, the connection node 390 may also be referred to as a "high density node." The concentration of sensors and circuits at a node, which characterizes a node as high density or low density, depends on the amount of information collected from sensors covering the portion of the knee at the node. For example, understanding rotational and patellofemoral motion requires more detailed sensor data, for example voltage sensor conductivity, than understanding extension movement in a single plane. Accordingly, a high density node, for example the connection 390, may be located at a position on the knee where such rotational and patellofemoral motion can be measured. A high density node may also be identified based on regions of the tension sensor array that are expected to experience significant conductive activity to change the shape of the wrap 350 or to transmit a large volume of signals. For example, a knee wrap includes a high density node on the lateral side to stiffen the lateral side. As another example, depending on the design considerations such as ACL instability or posterolateral instability, the knee wrap may have a low density node on the back of the knee and a high density a node laterally, medially, or around the patella.

Additionally, as discussed above, each circuit band anchoring the tension sensor array 310 (e.g., the lateral band 360, the superior band 370, and the inferior band 380) includes wiring or circuitry that connects tension sensors of the array 300 such that signals recorded by particular tension sensors may be transmitted to other tension sensors. Accordingly, a connection node located on a circuit band, such as the connection node 395, may be referred to as a primary circuit node. In some embodiments, the primary node represents a region of the tension sensor array 319 expected to experience the most significant conductive activity. The knee wrap 350 may further include secondary nodes (not shown), which are connection nodes that contain a secondary microprocessor or chip.

Movement of the knee may cause the geometry of the knee to dynamically change within the knee wrap. Accordingly, to maintain the form fitted design of the knee wrap, the knee wrap is designed to adjust its shape in real-time or near real-time to conform to the changing geometry of the knee. In some embodiments, the knee wrap includes one or more fluid chambers filled with an electroactive gel. Electroactive gels may be activated to stiffen particular portions of the brace, for example to dynamically improve joint stability or to prevent over extension of the joint. As described herein, fluid chambers are hollow pockets of varying shapes embedded into a wrap. A conductive wire sensor or thread may be attached to a fluid chambers to activate electroactive gels in the fluid chamber (or the fluid chamber itself) in response to signals from the controller to activate the electroactive gel or to dispense fluid in the chamber.

Figure 4:
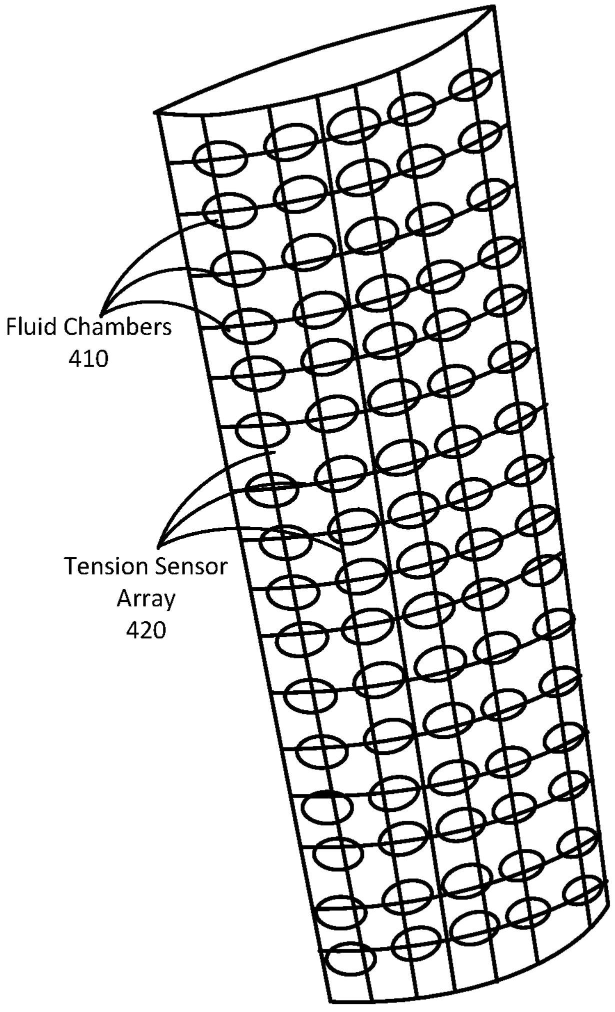
FIG. 4 is an illustration of a knee wrap with electroactive fluid chambers, according to one example embodiment.

FIG. 4 is an illustration of a knee wrap 400 with electroactive fluid chambers, according to one example embodiment. In the illustrated embodiment of FIG. 4, one or more fluid chambers 410 and a tension sensor array 420 are embedded in the knee wrap 400. The tension sensor array 420 may be structured as previously described, e.g., tension sensor array 210, 300. The fluid chambers 410 may be located at, or in proximity to, each connection node created of the tension sensor array 420. For example, the fluid chambers 410 may be located at the intersection of the vertically oriented tension sensors, e.g., 310, and the horizontally oriented tension sensors, e.g., 320. Alternately, the fluid chambers 410 may be located with the boundaries between parallel vertically oriented tension sensors, e.g., 310 and parallel horizontally oriented tension sensors, e.g., 320, where the vertically oriented tension sensors, e.g., 310, is adjacent to the horizontally oriented tension sensors, e.g., 330.

The number and location of fluid chambers 410 may be adjusted based on the joint covered by the wrap 400, the relative function and performance of the joint, or any other relevant factors. Further, the fluid chambers 410 may be self-contained or may be interconnected with each other within a closed system where fluid can flow at different ratees and levels between them to increase or decrease fluid density within each fluid chamber 410.

The electroactive gel within a fluid chamber 410 may be activated by an electrical signal or any other suitable electric stimuli. Upon activation, the electroactive gel undergoes a reaction that changes its physical properties, adjusting the pliability of the knee wrap itself by stiffening or softening the wrap 400 to accommodate various clinical scenarios. For example, activation of the electroactive gel in a fluid chamber 410 may cause the gel to transition into a semi-solid or solid state, reducing the pliability of the portion of the knee wrap surrounding the fluid chamber 410. In alternate embodiments, the fluid chambers 410 are filled with ferrofluid for dynamically adjusting of the geometry, orientation, location, or position of the wrap 400.

Accordingly, a controller embedded in the wrap 400, for example the controller 220, characterizes the movement of the knee based on signals received from the tension sensor array 210 and communicate electronic signals to one or more fluid chambers 410 to trigger the property-changing reaction in the electroactive gel within the fluid chambers 410. The controller 220 may apply the measurements recorded by the tension sensor array 420 to a machine learned model trained to identify possible injuries to the joint and the risk of those injuries occurring. The model may be trained using a training dataset collected from a population of patients, where the data is labeled with the injury experienced and the tension measurements that correlated with the injury. A second machine learned model, or alternatively the same model, may be used to identify adjustments to the pliability of the wrap 400, if any, that would prevent the injuries identified by the first model. The controller 220 may transmit signals for activating electroactive gel in one or more fluid chambers to change the shape or geometry of the wrap 400 according to the adjustments determined by the second model.

In some embodiments, a conductive thread connects each tension sensor of the array 420 to the controller 220 and connects the controller 220 to each of the fluid chambers. The conductive thread transmits tension changes from one tension sensor of the array 210 to another or to nodes where multiple tension sensors intersect. Based on measurements recorded by multiple sensors of the array 210, the controller 220 may generate instructions for activating electroactive gels in one or more fluid chambers to adjust the shape or geometry of the wrap 200 and transmit a current via the conductive thread to one or more fluid chambers to active the electroactive gel. In alternate embodiments, the electroactive gel may be activated by a voltage signal or an electromagnetic field. The amplitude of the current or voltage or the shape of an electromagnetic field generated in proximity to a fluid chamber causes electroactive gel in the fluid chamber to stiffen or soften, changing the geometry and structure of the knee wrap 200. For example, a valgus load applied to the knee places the medial collateral ligament (MCL) at risk of tearing. To prevent the MCL from tearing, the conductive thread transmits an electrical current to activate electroactive gels in fluid chambers on the medial side of the knee, causing the wrap 200 to stiffen and prevent from the MCL from tearing.

In some embodiments, a conductive thread connects fluid chambers 410 in a manner that enables the serial activation of the gels in the chambers. In such embodiments, electroactive gels within individual fluid chambers may be activated separately and independently at different times and in varying orders depending on the types of electroactive gels within the chambers, the position of the fluid chambers relative to the knee, or a combination thereof. Accordingly, the controller 220 may transmit signals to manage, activate, and deactivate electroactive gels in particular fluid chambers at different times or in different patterns.

In an alternate embodiment (not shown), the knee wrap is embedded with one or more strips filled with electroactive gel, also referred to as "stays." Each stay extends the length of the knee wrap from the superior circuit band to the inferior circuit band. The stays may be arranged in various geometries, shapes, and orientations depending on the joint covered by the plyowrap, the size of the plyowrap, the functionality and performance of the plyowrap, or any other relevant characteristics.

In addition to adjusting the geometry and pliability of the plyowrap based on the movement of the knee, a wearable brace 110 may also monitor and manage physiological properties of the user in real-time or near-real time. As discussed above, in addition to the tension sensor array, the knee wrap is embedded with a combination of sensers configured to monitor various physiological parameters that describe in part, or together as a whole, the patient's current health and fitness.

Figure 5:
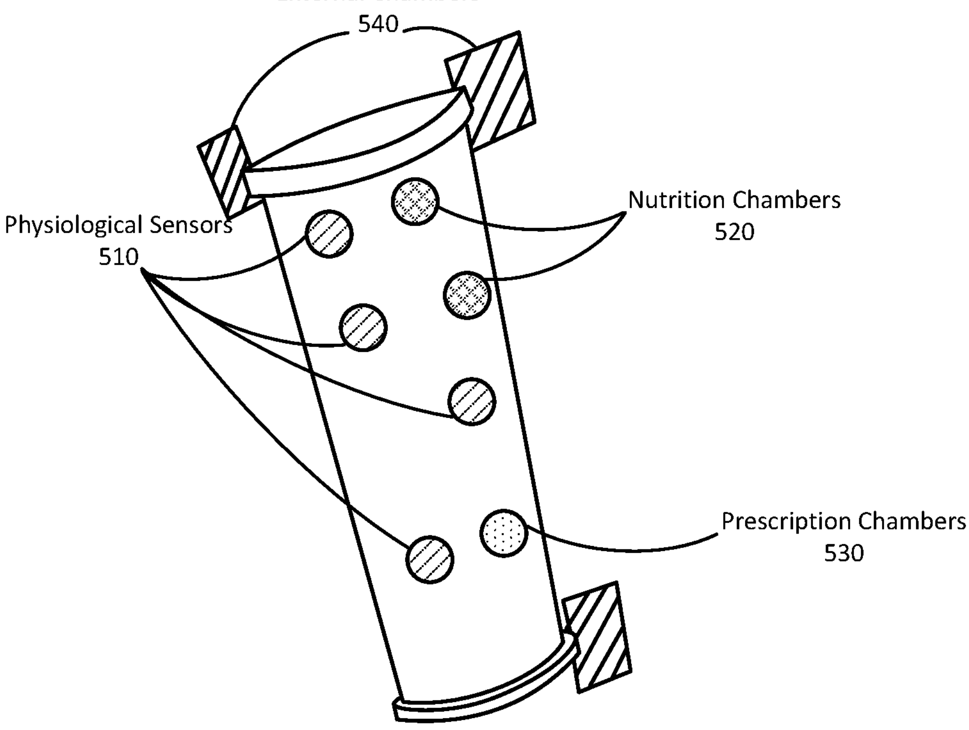
FIG. 5 is an illustration of a knee wrap with sensors configured to monitor physiological parameters and address changes in those parameters, according to one example embodiment.

FIG. 5 is an illustration of a knee wrap with sensors configured to monitor physiological parameters and detect changes in those parameters, according to one example embodiment. In the illustrated embodiment, the knee wrap 500 is embedded with a combination of physiological sensors 510, nutrition chambers 520, prescription chambers 530, and external chambers 540.

Physiological sensors 510 measure and detect changes in physiological properties such as in the temperature, $O_2$ saturation, glucose, energy, heat, elasticity, vibration, blood pressure, heart rate, conductivity, sensitivity, ultrasonic impedance, electromagnetic frequency, chemistry, sweat analytes, or any other suitable physical or physiological properties. In particular, electromagnetic physiological sensors may be used to detect changes in the electromagnetic current in the sleeve during static and movement activities of the body. Thermal physiological sensors may be used to detect temperature changes in the body based on measurements of the temperature of the skin surface. Ultrasonic sensors may be used to detect sound waves across the body using ultrasound sensors. Electromyograph sensors may be used to measure electrical signals generated by muscles during the movement of the joint. Based on measurements recorded by the physiological sensors 510, the controller 220 generates and transmits signals (e.g., an electric current) that cause nutrition chambers 520 or the prescription chambers 530 to deliver nutrients, medicine, or a combination thereof to the user.

In some embodiments, nutrition sensors (not shown) are embedded into the knee wrap 500 to detect changes in nutrient levels in the body, for example vitamins, minerals, glucose, proteins, carbohydrates and electrolytes. The nutrients as described may be substrates not subject to regulation, e.g., by the Food and Drug Administration (FDA), which can improve the health of an individual. For example, nutrition sensors may identify changes in the user's chemical balance based on sweat analysis to determine the user's nutritional needs. Based on the user's nutritional needs, the knee wrap 500 may deliver a nutrient supplement or transmit a notification to a patient device 130 with instructions for the user to take a nutritional supplement. Alternately, the nutrition sensors may be used to transmit regulatory approved substances, e.g., medical use substances.

The nutrition chambers 520 are fluid chambers containing a semi-solid or liquid substrate mixture of the nutrients, vitamins, and minerals that can be delivered to the joint or body parts surrounding the joint. The interior wall of nutrition chambers 520, which is positioned within in contact with the skin of the user may be permeable or semi-permeable to allow for the transdermal delivery of one or more of the nutrients contained in the fluid chamber. Described differently, the interior wall of the nutrient chamber 520 faces the skin of the user when the wrap 500 covers the joint. The interior wall of the nutrient chamber 520 may allow the nutrients within the chamber to diffuse onto the skin at a steady rate. For example, the controller 220 may determine that a user's sodium levels are decreasing at a steady rate based on measurements by the physiology sensors. Accordingly, the interior wall of the nutrient chamber 520 may allow for the steady transdermal delivery of sodium over an extended period of time.

In other embodiments, the permeability of the interior wall may be regulated in response to a signal from the controller 220 based on feedback from a physiological sensor or in response to a user-activated electronic signal. For example, a physiological sensor detects sweats analytes on the skin of a user indicating the user has low sodium levels. In response, the controller 220, or alternatively a connection node of the tension sensor array, transmits a signal (e.g., a current or voltage) that alters the permeability of the transdermal surface of one or more nutrient chambers to deliver nutrients to restore the sodium levels. In some embodiments, the transmitted signal directly transforms the transdermal surface of the nutrition chambers. The change in permeability may be maintained for a period of time as determined by the user or until the controller 220 receives feedback from the physiology sensor confirming restored nutrient levels. Alternatively, the period of time may be determined using a model, or any other suitable computational technique, trained to determine the amount of time for levels of a particular nutrient to rise.

In alternate embodiments, nutrients stored within the nutrition chamber 520 are delivered by a transcutaneous delivery pump. Such a delivery pump may be activated electronically by a signal from the controller generated in response to a measurement by physiological sensors 510. Alternatively, the delivery pump may be activated manually, for example using an activation switch, a pump, a button on the microprocessor, or via a remote signals from a mobile application on a patient device 130 or a provider device 140. For example, if a user running with the knee wrap 500 recognizes that they are sweating profusely, they may manually activate the delivery pump of a nutrition chamber 520 containing an electrolyte mixture to deliver the mixture. In embodiments involving a delivery pump, the nutrient is applied to the skin of a user in doses in response to a signal from the controller. Returning to the example involving the nutrition chamber 520 containing sodium, when physiological sensors 510 measure a sodium level below a threshold, the controller may generate and transmit a signal triggering the transdermal or transcutaneous delivery of the nutrients in the chamber 520 in real-time.

Prescription chambers 530 are fluid chambers containing a semi-solid or liquid mixture of medications that may be used to treat medical conditions that are detected by the physiological sensors 510 or are known to afflict the user. For example, if a user is diabetic, the physiological sensors 810 detect low levels of transcutaneous glucose which cause the controller 510 to generate and transmit a signal for the prescription chamber 530 to apply glucose transdermally or trascutaneously, for example using a delivery pump. As another example, a prescription chamber 530 may contain a pain medication, which is dispensed by the prescription chamber in response to user feedback or physiological measurements indicating that the user is in pain. In embodiments where changes in the Cartesian grid created by the tension sensor array 510 indicate a pattern of motion indicative of an injury (e.g., a knee dislocation), the controller 220 may automatically trigger prescription chambers to administer a pain medication or activate electroactive fluids to immobilize the knee like a splint.

The techniques discussed above with regards to transdermal and transcutaneous delivery of nutrients may also be applied here for the transdermal and transcutaneous delivery of medication.

Nutrition chambers 520 and prescription chambers 530 are structurally consistent with the fluid chambers filled with electroactive fluids described above with regards to FIG. 4. Additionally, nutrition chambers 520 and prescription chambers 530 may include mechanical components that allow a user to refill the chambers during use or between uses of the knee wrap 500. In one embodiment, the chambers 520 and 530 include a value where a user can add nutrients or medications to the chamber. In alternate embodiments, the chambers 520 and 530 may include an injection port where a user can fill the chamber with nutrients or medications.

In some embodiments, medications in the prescription chambers 530 may be applied in real-time or near real-time in response to measurements by the physiological sensors 510. Such real-time or near real-time responses allow the knee wrap 500 to accommodate or adjust to changes in the physiological state of the joint covered by the knee wrap 500 while in use or in motion. For example, a user running a marathon may get dehydrated in the 12$^{th}$ mile, causing their potassium levels to drop. Physiology sensors 510 may detect the lowered potassium levels based on sweat analytes or the skin surface. When the potassium levels drop below a threshold level, the controller 220 transmits a signal causing the electric activation of a pump to deliver potassium to the user. Alternatively, the controller 220 may transmit a notification or reminder to a patient device 130 instructing the user to manually activate the pump. The description above may be applied to any suitable medication, vitamin, or nutrients, for example sodium, sugar, glucose, vitamin C, vitamin D, an electrolyte mixture, or some other combination of the medication, vitamins, and nutrients.

The knee wrap 500 further includes external chambers 540 coupled to the exterior of the knee wrap 500 using any suitable attachment technique or mechanism. In some embodiments, the external chambers 540 contain solid medications, vitamins, or other nutrients. The external chambers 540 may also store liquid medications, mixtures of vitamins, or mixtures of nutrients. During use of the knee wrap 500, a user may access the external chambers 540 to consumer the contents of the chambers or to fill a chamber of the knee wrap. External chambers 540 may be designed in any suitable geometry.

Figure 6A:
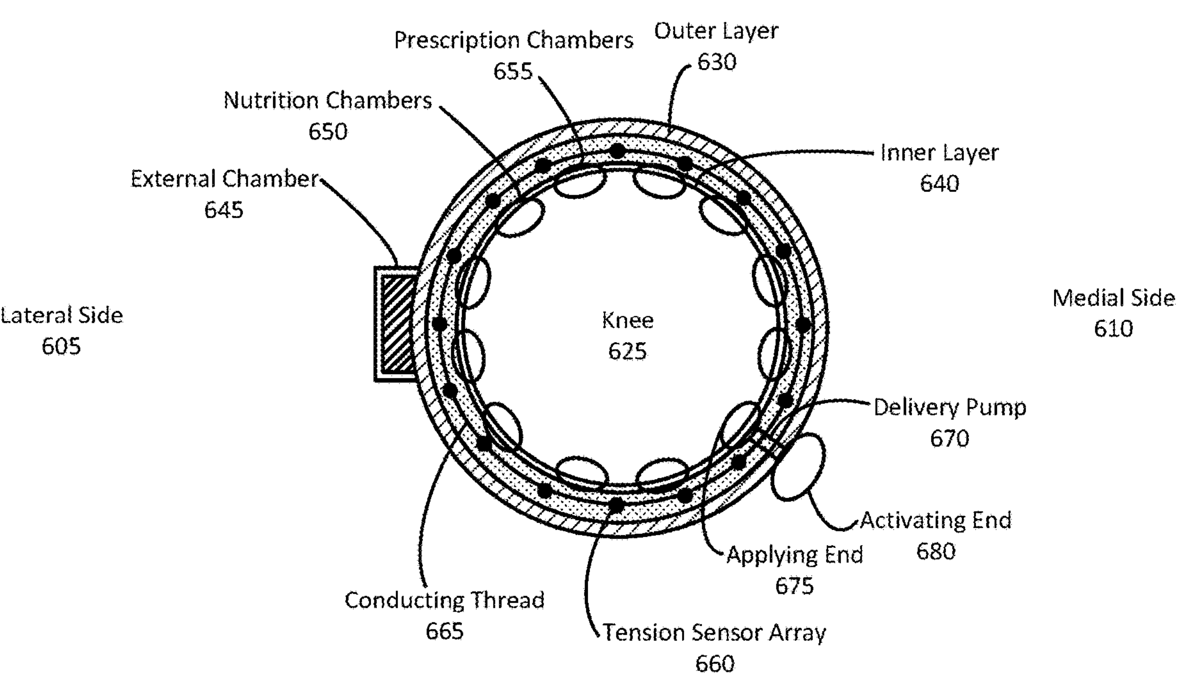
FIG. 6A is an illustration of a cross-section of a knee wrap that includes an outer layer and an inner layer, according to one example embodiment.

FIG. 6A is an illustration of a cross-section of a knee wrap that includes an outer layer and an inner layer, according to one example embodiment. In the illustrated embodiment, the wrap 600 covers the knee 625 of a user. For the sake of description, the lateral side 605, the medial side 610, the anterior side 615, and the posterior side 620 are labeled in FIG. 6A. An external chamber 645, an embodiment of the external chambers 540, is coupled to the outer layer. Fluid chambers containing liquid or semi-solid substrates to be delivered to the user, for example the nutrient chambers 650 and prescription chambers 655, are embedded into the inner layer 640 such that the fluid chambers contact the skin of the joint and body parts surrounding the joint. Because the inner layer 640 and components embedded into the inner layer 640 contact the skin of the user, the inner layer 640 may be slip resistant or include a slip resistant lining on the surface contacting the skin.

In the illustrated embodiment of FIG. 6A, the tension sensor array 660, which is an embodiment of the tension sensor array 210, and the conductive thread 665 connecting the sensors of the array 660 are positioned between the outer layer 630 and the inner layer 640. In alternate embodiments, the tension sensor array 210 may be embedded into the material of outer layer 630 or the inner layer 640.

Figure 6B:
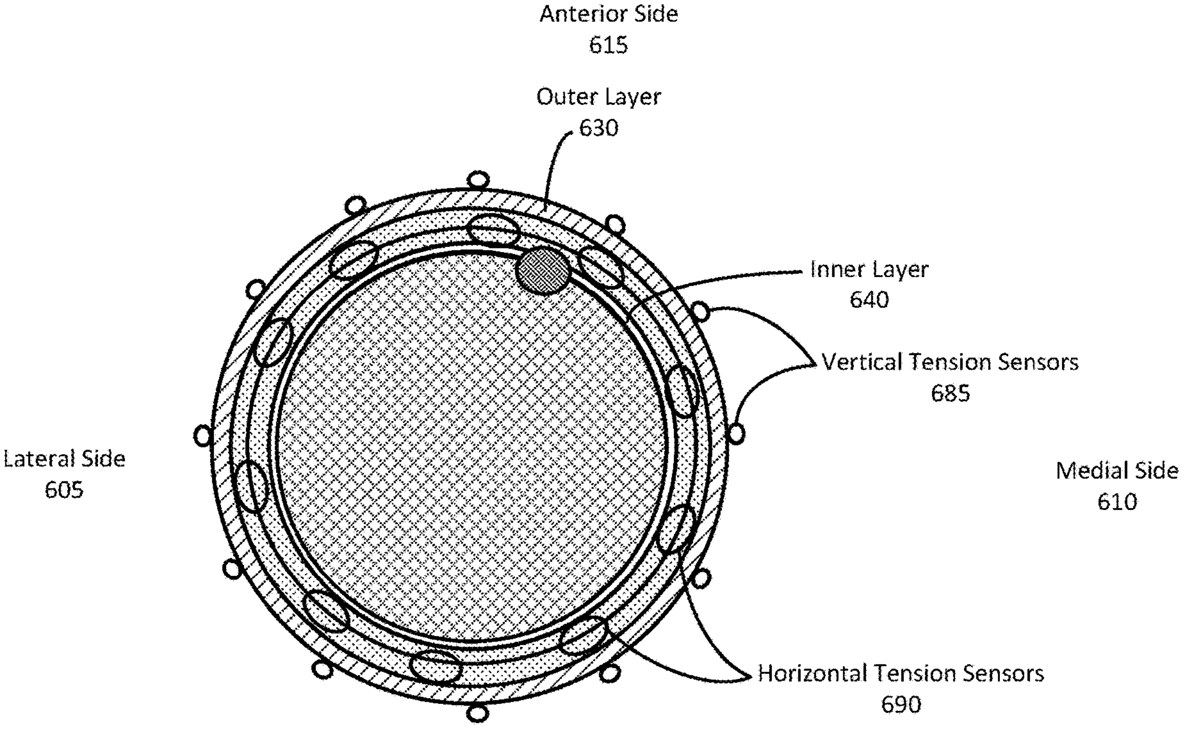
FIG. 6B is an illustration of a cross-section of a knee wrap that includes an outer layer, an inner layer, and an alternate configuration of the tension sensor array, according to an example embodiment.

In the illustrated embodiment, the delivery pump 670, which facilitates transcutaneous delivery of nutrients, medication, or vitamins, is embedded in both the outer layer 630 and the inner layer 640. The applying end 675 of the pump 670 extends through the inner layer 640 to contact the skin of the user. As described herein, the applying end 675 is the end of the pump 670 that delivers the contents of the pump. In the illustrated embodiment of FIG. 6A, the opposite end, the activating end 680 of the pump 670 extends through the outer layer 650 such that the user may access the activating end 680 to manually activate the pump to deliver its contents. In embodiments (not shown) where the pump 670 is electrically activated, the activating end may only extend into contact with the conducting thread 655 such that the controller 620 may communicate electronic signals via the thread 655 to activate the pump. I FIG. 6B is an illustration of a cross-section of a knee wrap that includes an outer layer, an inner layer, and an alternate configuration of the tension sensor array, according to an example embodiment. Consistent with the description in FIG. 6A, the knee wrap 680 illustrated in FIG. 6B includes an outer layer 630 and an inner layer 640. Recalling the description above of the tension sensor array 210, tension sensors may be oriented along a vertical axis or along a horizontal axis of the wrap 680. Returning now to the embodiment illustrated in FIG. 6B, vertical tension sensors 685 are embedded into the outer layer 630 and horizontal tension sensors 690 are embedded between the outer layer 630 and the inner layer 640.

Additionally, in the embodiment illustrated in FIG. 6B, nutrition chambers, prescription chambers, and fluid chambers containing electroactive gels are embedded between the inner layer 640 and the outer layer 630. In such embodiments, the inner layer 640 is permeable to facilitate the diffusion and delivery of contents within the nutrition chambers and prescription chambers onto the skin of the user. The inner layer 640 is additionally pliable to facilitate changes in the geometry of the wrap 680 caused by the activation of the electroactive gels within fluid chambers.

In some embodiments, fluid chambers containing electroactive gels are embedded in each of the inner layer 640 and the outer layer 630. In such embodiments, the fluid chambers of the inner layer 640 may be connected to the controller by a separate conductive thread and control circuitry than the fluid chambers of the outer layer 630. Accordingly, a controller may generate signals with instructions for the inner layer 640 to change its structure or geometry differentially from the outer layer. For example, electroactive gels in fluid chambers of the outer layer 630 may be activated to stiffen the outer layer 630 to protect against injury or impact, while electroactive gels in fluid chambers of the inner layer 640 may be activated to soften the inner layer 630 to dampen the force on the joint. The inner layer 640 may also be made from fabrics, materials, or layers of various fabrics to dampen forces on the joint.

IV. Computing Machine Architecture

Figure 7:
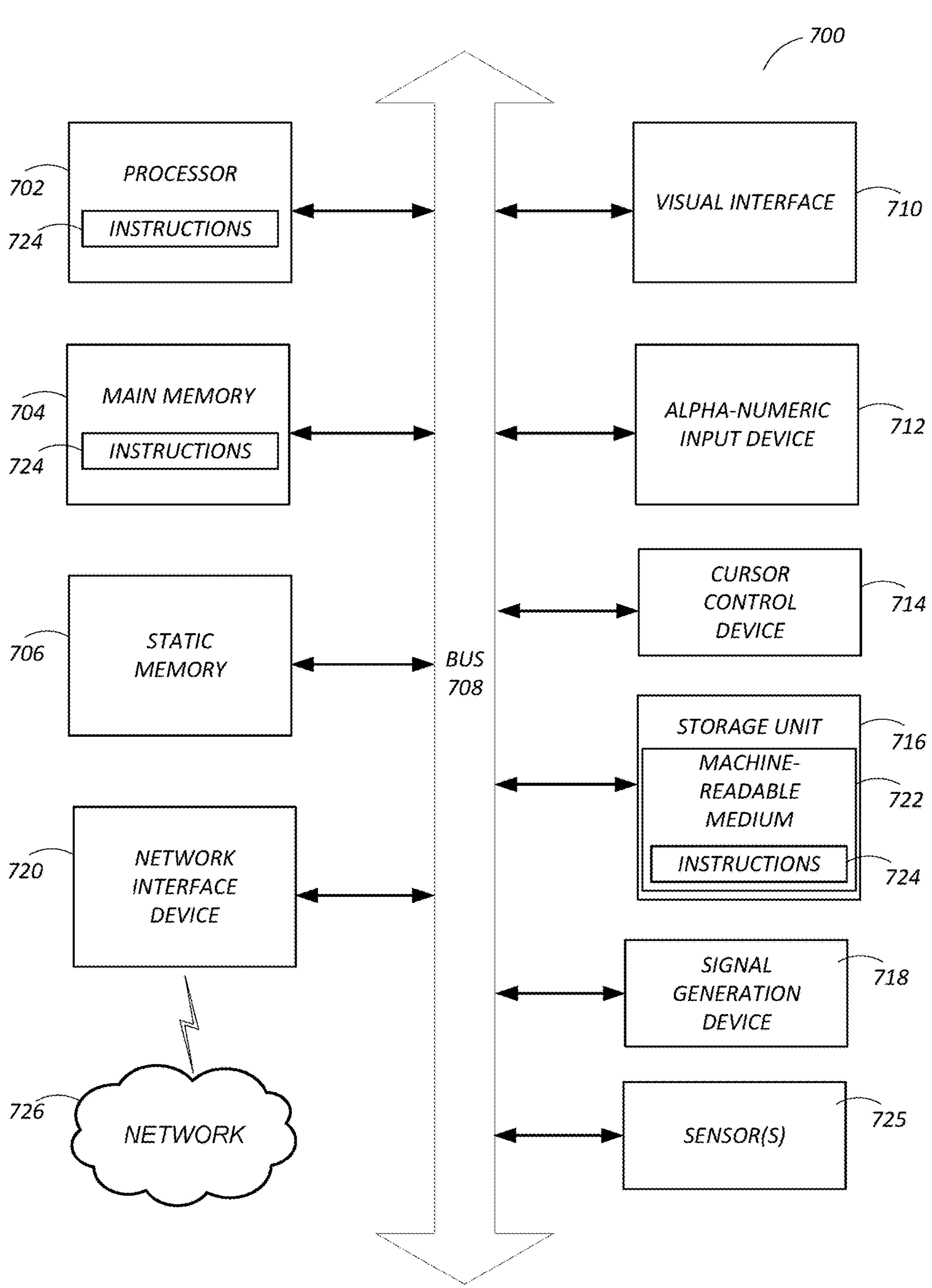
FIG. 7 is a block diagram illustrating components of an example machine able to read instructions from a machine-readable medium and execute them in a processor (or controller), according to one example embodiment.

FIG. 7 is a block diagram illustrating components of an example machine able to read instructions from a machine-readable medium and execute them in a processor (or controller), according to one embodiment. Specifically, FIG. 7 shows a diagrammatic representation of a machine in the example form of a computer system 800 within which program code (e.g., software) for causing the machine to perform any one or more of the methodologies discussed herein may be executed. The tablet scribe device 110 may include some or all of the components of the computer system 700. The program code may be comprised of instructions 724 executable by one or more processors 802702 In the tablet scribe device 110, the instructions may correspond to the functional components described in FIGS. 2-6B.

While the embodiments described herein are in the context of the tablet scribe device 110, it is noted that the principles may apply to other touch sensitive devices. In those contexts, the machine of FIG. 7 may be a server computer, a client computer, a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 724 (sequential or otherwise) that specify actions to be taken by that machine. Further, while only a single machine is illustrated, the term "machine" shall also be taken to include any collection of machines that individually or jointly execute instructions 724 to perform any one or more of the methodologies discussed herein.

The example computer system 700 includes one or more processors 702 (e.g., a central processing unit (CPU), one or more graphics processing units (GPU), one or more digital signal processors (DSP), one or more application specific integrated circuits (ASICs), one or more radio-frequency integrated circuits (RFICs), or any combination of these), a main memory 704, and a static memory 706, which are configured to communicate with each other via a bus 708. The computer system 700 may further include visual display interface 710. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 710 may include or may interface with a touch enabled screen. The computer system 700 may also include alphanumeric input device 712 (e.g., a keyboard or touch screen keyboard), a cursor control device 714 (e.g., a mouse, a trackball, a joystick, a motion sensor, or other pointing instrument), a storage unit 716, a signal generation device 718 (e.g., a speaker), and a network interface device 720, which also are configured to communicate via the bus 708.

The storage unit 716 includes a machine-readable medium 722 on which is stored instructions 724 (e.g., software) embodying any one or more of the methodologies or functions described herein. The instructions 724 (e.g., software) may also reside, completely or at least partially, within the main memory 704 or within the processor 702 (e.g., within a processor's cache memory) during execution thereof by the computer system 700, the main memory 704 and the processor 702 also constituting machine-readable media. The instructions 724 (e.g., software) may be transmitted or received over a network 726 via the network interface device 720.

While machine-readable medium 722 is shown in an example embodiment to be a single medium, the term "machine-readable medium" should be taken to include a single medium or multiple media (e.g., a centralized or distributed database, or associated caches and servers) able to store instructions (e.g., instructions 724). The term "machine-readable medium" shall also be taken to include any medium that is capable of storing instructions (e.g., instructions 724) for execution by the machine and that cause the machine to perform any one or more of the methodologies disclosed herein. The term "machine-readable medium" includes, but not be limited to, data repositories in the form of solid-state memories, optical media, and magnetic media.

The computer system 700 also may include the one or more sensors 725. Also note that a computing device may include only a subset of the components illustrated and described with FIG. 7. For example, an IoT device may only include a processor 702, a small storage unit 716, a main memory 704, a visual interface 710, a network interface device 720, and a sensor 725.

V. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A wearable device comprising: a wrap configured to be pliable and further comprising: a first plurality of fluid chambers integrated into the wrap that is configured to conform to a shape of a joint of a user, each fluid chamber of the first plurality of fluid chambers comprising an electroactive gel, the electroactive gel being activatable to adjust a pliability of the wrap; and a second plurality of fluid chambers integrated into the wrap, an interior wall of each fluid chamber of the second plurality of fluid chambers configured to contact a skin area of the user, the interior wall of each fluid chamber of the second plurality of fluid chambers facilitating transdermal delivery of one or more nutrients contained in each fluid chamber of the second plurality of fluid chambers to the user; an array of tension sensors embedded into the wrap across at least one horizontal axis and at least one vertical axis of the wrap, each tension sensor comprising a flexible wire configured to stretch or compress the wrap to generate a signal corresponding to a movement of the joint; and one or more force sensors located at each intersection between tension sensors on a horizontal axis and tension sensors on a vertical axis, the one or more force sensors configured to collect force measurements based on the movement of the joint; and a controller, coupled with the wrap, the controller configured to: receive signals generated by the array of tension sensors the received signals corresponding to the movement of the joint and force measurements collected by the one or more force sensors; generate a Cartesian map of the joint describing changes in a shape of the joint during the movement of the joint; and generate a signal to activate the electroactive gel in the first plurality of fluid chambers to adjust the pliability of the wrap based on an analysis of the Cartesian map.

2. The wearable device of claim 1, wherein each tension sensor of the array of tension sensors is anchored in a horizontal plane by a lateral band positioned along a length of a vertical axis of the wearable device and is anchored in a vertical plane by a superior lateral band and an inferior lateral band, the superior lateral band and the inferior lateral band positioned along horizontal axes on either ends of the wearable device.

3. The wearable device of claim 2, wherein the inferior lateral band or the superior lateral band comprise one or more of: electrical components configured to transmit signals recorded by a first tension sensor of the array of tension sensors to one or more other tension sensors of the array of tension sensors; and one or more additional sensors configured to measure movement of an area of the joint of the user covered by the superior lateral band or inferior lateral band.

4. The wearable device of claim 1, further comprising: at least one physiological sensor embedded into the wrap, the at least one physiological sensor configured to measure physiological parameters corresponding to the user.

5. The wearable device of claim 4, wherein each fluid chamber of the second plurality of fluid chambers further comprises:

a pump configured to facilitate transcutaneous delivery of the one or more nutrients to the user in response to signals corresponding to the physiological parameters.

6. The wearable device of claim 1, further comprising: a conductive thread coupling the array of tension sensors and the controller and coupling the controller with the first plurality of fluid chambers, the conductive thread configured to transmit signals from the controller to activate the electroactive gels in one or more fluid chambers of the first plurality of fluid chambers to adjust the pliability of the wrap.

7. The wearable device of claim 1, further comprising: an array of voltage sensors embedded into the wrap across a horizontal axis and a vertical axis of the wrap, wherein each voltage sensor of the array of voltage sensors is configured to measure changes in a voltage caused by movements of the joint; and a conductive thread connecting each voltage sensor of the array of voltage sensors, the conductive thread configured to transmit voltage changes measured by a first voltage sensor to other voltage sensors of the array of voltage sensors.

8. A knee brace comprising: a wrap configured to be pliable and comprising: a first plurality of fluid chambers integrated into the wrap that is configured to conform to a shape of a knee of a user, the first plurality of fluid chambers having an electroactive gel, the electroactive gel being activatable to adjust a pliability of the wrap; and a second plurality of fluid chambers integrated into the wrap comprising an interior wall, the second plurality of fluid chambers structured and configured to contract a surface of the knee, the interior walls of the second plurality of fluid chambers structured to facilitate transdermal delivery of one or more nutrients contained in the second plurality of fluid chambers; tension sensors embedded into the wrap and arranged in an array across at least one horizontal axis and at least one vertical axis of the wrap, each tension sensor comprising a flexible wire configured to stretch or compress to generate a signal corresponding to changes in geometry in response to movements of the knee; one or more force sensors located at each intersection between tension sensors on the at least one horizontal axis and tension sensors on the at least one vertical axis, the one or more force sensors is configured to collect force measurements responsive to movement of the knee; and a controller coupled with the wrap, the controller configured to: receive signals generated by the tension sensors corresponding to the movement the knee and the force measurements collected by the one or more force sensors; generate a mapping of the knee corresponding to changes in a shape of the knee during the movement of the knee; and generate a signal to activate the electroactive gel in the first plurality of fluid chambers to adjust the pliability of the wrap based on an analysis of the mapping of the knee.

9. The knee brace of claim 8, wherein each tension sensor in the array is anchored in a horizontal plane by a lateral band positioned along a length of a vertical axis of the knee brace and is anchored in a vertical plane by a superior lateral band and an inferior lateral band, the superior lateral band and the inferior lateral band positioned along horizontal axes on either ends of the knee brace.

10. The knee brace of claim 9, wherein the inferior lateral band or the superior lateral band comprises at least one of:

electrical components configured to transmit signals recorded by a first tension sensor of the array to one or more other tension sensors of the array; and one or more additional sensors configured to measure movement of an area of the knee covered by the superior lateral band or inferior lateral band.

11. The knee brace of claim 8, further comprising at least one physiology sensor embedded into the wrap, the at least one physiology sensor configured to measure a physiological parameter of one or more physiological parameters of the user.

12. The knee brace of claim 11, wherein each fluid chamber of the second plurality of fluid chambers further comprises a pump configured to facilitate transcutaneous delivery of the one or more nutrients to the user in response to signals associated with the one or more physiological parameters of the user.

13. The knee brace of claim 8, further comprising a conductive thread coupling the array of tension sensors with the controller and coupling the controller to the fluid chambers, the conductive thread configured to transmit electrical signals from the controller to activate the electroactive gels in the first plurality of fluid chambers to adjust the pliability of the knee wrap.

14. The knee brace of claim 8, further comprising: an array of voltage sensors embedded into the wrap across the at least one horizontal axis and the at least one vertical axis of the wrap, each voltage sensor of the array of voltage sensors configured to measure changes in a voltage caused by movements of the knee; and a conductive thread connecting each voltage sensor of the array of voltage sensors, the conductive thread configured to transmit voltage changes measured by a first voltage sensor to other voltage sensors of the array of voltage sensors.

15. A wearable device comprising: a pliable wrap comprised of a plurality of fluid chambers coupled together to structure the wrap that is configured to conform to a shape of a joint of a user, each fluid chamber of the plurality of fluid chambers comprising an electroactive gel, the electroactive gel being activatable to adjust a pliability of the wrap; an array of tension sensors embedded into the wrap across one or more horizontal axes and one or more vertical axes of the wrap, each tension sensor comprising a flexible wire configured to generate a signal describing a movement of the joint covered by the wrap by stretching or compressing as a geometry of the wrap changes; one or more force sensors located at each intersection between tension sensors on a horizontal axis and tension sensors on a vertical axis, the one or more force sensors is configured to collect force measurements based on the movement of the joint; and a controller coupled with the wrap, the controller configured to: receive signals generated by the array of tension sensors describing the movement of the joint and force measurements collected by the one or more force sensors; generate a mapping of the joint describing changes in a shape of the joint during the movement of the joint; and generate a signal to activate the electroactive gel in the plurality of chambers to adjust the pliability of the wrap based on an analysis of the mapped joint.

16. The wearable device of claim 15, further comprising at least one physiology sensor embedded into the wrap, each physiology sensor configured to measure a physiological parameter of one or more physiological parameters of the user.

17. The wearable device of claim 16, wherein each fluid chamber of the plurality of fluid chambers further comprises a pump configured to facilitate transcutaneous delivery of one or more nutrients to the user in response to signals associated with the one or more physiological parameters of the user.

18. The wearable device of claim 15, wherein each tension sensor of the array of tension sensors is anchored in a horizontal plane by a lateral band positioned along a length of a vertical axis of the wearable device and is anchored in a vertical plane by a superior lateral band and an inferior lateral band, the superior lateral band and the inferior lateral band positioned along horizontal axes on either ends of the wearable device.

19. The wearable device of claim 15, further comprising a conductive thread coupling the array of tension sensors with the controller and coupling the controller with the plurality of fluid chambers, the conductive thread configured to transmit electrical currents from the controller to activate the electroactive gels in one or more fluid chambers of the plurality of fluid chambers to adjust the pliability of the wrap.

20. The wearable device of claim 15, further comprising: an array of voltage sensors embedded into the wrap across one or more horizontal axes and one or more vertical axes of the wrap, wherein each voltage sensor of the array of voltage sensors is configured to measure changes in a voltage caused by movements of the joint; and a conductive thread coupling each voltage sensor of the array of voltage sensors, the conductive thread configured to transmit voltage changes measured by a first voltage sensor to one or more other voltage sensors of the array of voltage sensors.

* * * * *